United States Patent [19]

Li et al.

[11] Patent Number: 4,971,803

[45] Date of Patent: Nov. 20, 1990

[54] LAMELLAR VESICLES FORMED OF CHOLESTEROL DERIVATIVES

[75] Inventors: Ming P. Li; John D. Baldeschwieler, both of Pasadena, Calif.

[73] Assignee: California Institute of Technology, Pasadena, Calif.

[21] Appl. No.: 259,453

[22] Filed: Oct. 17, 1988

Related U.S. Application Data

[63] Continuation of Ser. No. 720,957, Apr. 8, 1985, abandoned.

[51] Int. Cl.$^5$ .................... A61K 37/22; A61K 47/00
[52] U.S. Cl. ...................................... 424/450; 514/772
[58] Field of Search ............ 260/397.2; 552/541, 552/544; 424/450; 514/772

[56] References Cited

U.S. PATENT DOCUMENTS

| | | | |
|---|---|---|---|
| 4,145,357 | 3/1979 | Ochi et al. | 260/397.2 |
| 4,235,792 | 11/1980 | Hsia et al. | 260/397.2 |
| 4,599,330 | 7/1986 | Boris et al. | 260/397.2 |
| 4,601,855 | 7/1986 | Rappoldt et al. | 260/397.2 |

OTHER PUBLICATIONS

Chemical Abstracts 74:54100d (1971) Ahmad et al.
Chemical Abstracts 82:43651y (1975) Ahmad et al.
Chemical Abstracts 84:133066g (1976) Hikino et al.
Chemical Abstracts 92:53745c (1980 Ayenger et al.
Chemical Abstracts 97:194851z (1982) Brackerhoff et al.
Chemical Abstracts 101:19360u (1984) Mishima et al.
Chemical Abstracts 103:11328j (1985) Patel et al.
Patel, K. R., Li, M. P., Schuh, J. R. and Baldeschwieler, J. D. *Biochim. Biophs*, Acta. 797, 20–26 (1984).
Davis, M. J. *Chem. Soc.* 178 (1962).
Fry, D. W., White, J. C. and Goldman, I. D. *Anal. Biochem.* 90, 809–815 (1978).
Guilmette, R. A., Cerny, E. A., Rahman, Y. E. *Life Sci.* 22, 313–318 (1978).
Brokerhoff, H. and Ramsammy, L. *Biochim. Biophys.* Acta 691, pp. 227–232 (1982).

Primary Examiner—Douglas W. Robinson
Assistant Examiner—Kevin Weddington
Attorney, Agent, or Firm—Marvin E. Jacobs

[57] ABSTRACT

Closed, unilamellar vesicles are spontaneously formed by adding a cholesteryl compound substituted with a hydroxyl terminated polyethylene oxide containing 1 to 4 ethylene oxide groups to a polar liquid. Multilamellar vesicles are formed by sonicating a cholesteryl compound containing polyethylene oxide or polyamine side-chains. The vesicles can be utilized to dispense polar, non-polar or ampholphilic compounds.

13 Claims, 2 Drawing Sheets

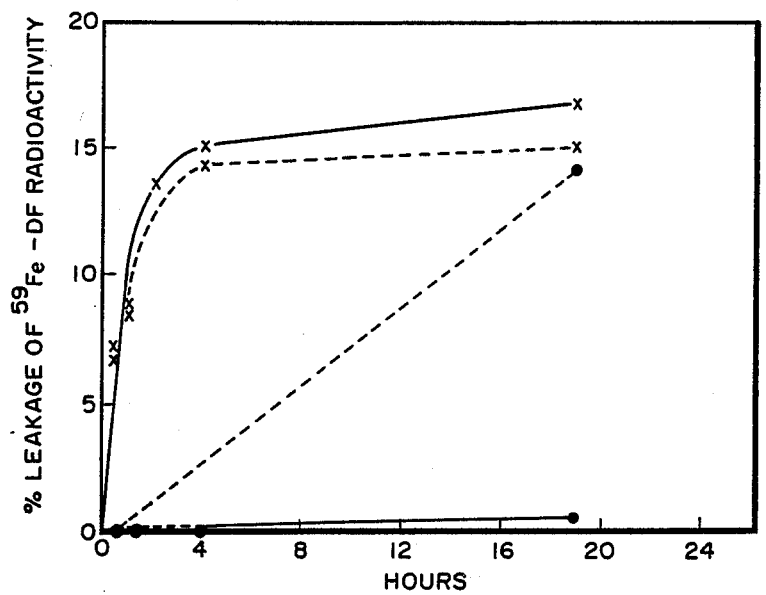

Fig. 4. STABILITY OF SONICATED AND UNSONICATED TRIETHOXYCHO-LESTEROL LIPOSOMES. x———x, SONICATED LIPOSOMES, LEAKAGE IN PHOSPHATE-BUFFERED SALINE; x------x, SONICATED LIPOSOMES, LEAKAGE IN SERUM; ●------●, UNSONICATED LIPOSOMES, LEAKAGE IN SERUM; ●———●, UNSONICATED LIPOSOMES, LEAKAGE IN PHOSPHATE-BUFFERED SALINE.

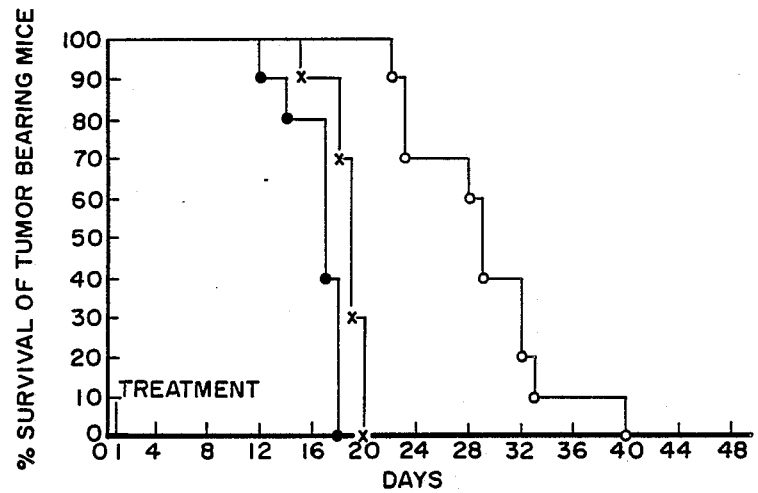

Fig. 5. THERAPEUTIC EFFECT OF TRIETHOXYCHOLESTEROL UNSONICATED LIPOSOME-ENCAPSULATED METHOTREXATE ON SURVIVAL OF MICE BEARING HEPATOMA 129 ASCITES TUMOR. ●, UNTREATED CONTROL; x, UNENCAPSULATED METHOTREXATE (3mg/kg) BY INTRAPERITONEAL ROUTE; o, TRIETHOXYCHOLE-STEROL UNSONICATED LIPOSOME-ENCAPSULATED METHOTREXATE (2.5mg/kg) BY INTRAPERITONEAL ROUTE.

LAMELLAR VESICLES FORMED OF CHOLESTEROL DERIVATIVES

ORIGIN OF THE INVENTION

This invention was made in the course of work performed under Grant No. GM 2111109 with the National Institute of Health.

This is a continuation of application Ser. No. 720,957, filed Apr. 8, 1985, now abandoned.

BACKGROUND OF THE INVENTION

This invention relates to substituted cholesterol derivatives and, more particularly, to unilamellar and multilamellar vesicles as encapsulants for polar compounds, particularly, therapeutical agents.

Encapsulation is utilized to isolate sensitive materials from chemically aggressive environments and/or to control release of the encapsulated material at a particular time at a specified rate or at a specified site of delivery. Encapsulation can be utilized to dispense household products such as insecticides, cosmetic products such as topical products, chemical warfare agents and pharmaceuticals. Any material compatible with the encapsulant can be processed into an encapsulated form.

The microencapsulation of drugs holds great potential for increasing the efficacy of pharmaceutical therapies while reducing unwanted systemic effects by targeting specific organs for drug release. Numerous studies have employed phospholipids, both as model membranes and as carriers for a variety of biologically active materials. For example, enzymes, chelating agents, viral nucleic acids, anti-tumor drugs, antifiotics, immunogens and hormones have all been successfully encapsulated with liposome systems. Phospholipid-containing systems are inherently attractive for encapsulation since they contain lipids analogous to those found in cell membrane and thus are stabilized by the same forces that maintain cell integrity in vivo. However, these lipids are also susceptible to enzymatic degradation and may display antigenic surfaces, which can give rise to a subsequent immunological response. A major obstacle to the use of circulating liposome carriers has been their rapid uptake and removal by the liver.

The development of artificial materials for encapsulation offers an alternative approach to resolving problems of liposome instability, while increasing the versatility of these systems. Although most liposome studies have been conducted with diacyl phosphatidylcholine bilayers, a number of investigators have reported liposome formation using other amphiphiles, such as dihexadecylphosphate. Non-bilayer forming lipids, such as cholesterol or phosphatidylethanolamine have been found to form closed vesicles upon the addition of other compounds such as ceramides and fatty acids, nonionic detergents, bile acids and lysophosphatidylcholine. Bilayered structures have also been formed by single lipid molecules, containing two polar groups connected by an alkyl moiety.

Several approaches have been taken to deliver selectively liposome encapsulated materials to specific organs or types of tissues. Modification of lipid acyl groups to alter the liposome phase transition temperature can induce the preferential release of encapsulated materials at sites of inflammation and infection where the pH is slightly below the physiological level. Alternatively, one can change the surface properties of liposomes so that they will interact specifically with cell surface groups on the targeted tissue. Successful demonstrations of this approach include the attachment of tumor cell specific antibodies to a vesicle surface and incorporation of lipid containing charged groups or carbohydrates which alter the liposome surface and tissue distribution.

These artificial materials were based on the use of fluid, acyl chains and were mainly based on phospholipid containing systems. Encapsulation was accomplished by extensive sonication to form multilayer vesicles. Sonication results in heating the vesicles which results in deactivation of thermally sensitive materials.

STATEMENT OF THE INVENTION

Closed liposome vesicles having low leakage rates have been formed in accordance with the invention. The liposomes are formed from a non-phospholipid, non-acyl substituted cholesterol. A simple cholesterol modified with a single side chain is found to spontaneously form a unilamellar vesicle structure of small unit size without sonication. This is pharmacologically advantageous in providing a lower rate of uptake in the liver and higher rate of uptake by tumors.

The absence of sonication permits encapsulation of thermally labile materials. Sonication results in the formation of larger multilamellar vesicles. Other modified cholesterol derivatives of the invention are found to form liposomes and to have a range of leakage rates providing the ability to form a vesicle of predetermined leakage rate by blending with natural liposome forming materials such as phospholipids.

Hydration of the cholesterol derivatives of the invention results in the formation of stable, rigid, bilayer-like structure capable of encapsulating polar compounds. Lipid soluble, non-polar compounds dissolve in the bilayer and amphophilic compounds partition between the encapsulated polar liquid and the membrane. Studies on the stability and tissue distribution of these vesicles indicate that the modified cholesterol compounds of the invention intrinsically stabilize vesicles without affecting their in vivo tissue distribution. In vivo studies of injection of an antitumor drug into mice bearing hepatoma ascites results in doubling of survival time relative to untreated mice and to those receiving unencapsulated drug. Studies of the efficacy of anti-fungal drugs indicate that only the drug encapsulated with the modified cholesterol of the invention could be given in vivo in sufficient concentration to eliminate colony forming units from the spleen.

The rigid bilayer structures are formed from a molecule having a rigid non-polar hydrocarbon parent structure containing a single, polar side chain. When the molecules are hydrated with water the flexible lipophilic side chains complex with adjacent molecules to form a bilayer with the rigid non-polar structure oriented to the interior region of the bilayer. The flexible, polar side chains are sufficient length to fill the bipolar volume.

The preferred liposome forming molecules utilized in the invention have a central non-polar cholesterol structure containing a hetero-alkyl side chain containing from 2 to 8 carbon atoms interspersed with from 2 to 5 hetero-atom groups selected from O, N and the like. The modified cholesterol derivatives can be selected from compounds of the formula:

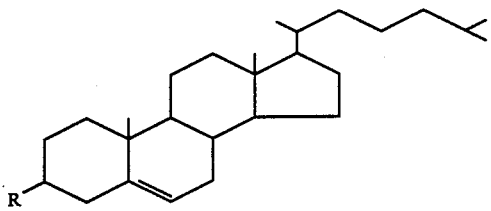

where R is a group selected from:

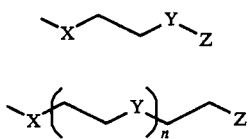

where X is selected from O or —NH, Y is X or $CH_2$ and Z is a terminal polar group selected from —OH or —$NH_2$ and n is an integer from 1 to 4.

The modified cholesterol compounds are prepared by reaction of a solution of cholesteryl P-toluenesulfonate in solvent with an excess of glycol or amine precursor of the side chain under reflux with stirring until the reaction is complete. Solvent is removed under vacuum and the reaction mixture is diluted with water and extracted with ether. The organic phase is washed with aqueous sodium carbonate, water and then dried to recover a viscous syrup in high yield which can be used directly without further purification.

Vesicles containing an encapsulated material are prepared by adding an aqueous solution of the material to be encapsulated to a dried film of modified cholesterol material. Unencapsulated material is removed by centrifugation. Some of the vesicles are sonicated.

These and many other features and attendant advantages of the invention will become apparent as the invention becomes better understood by reference to the following detailed description when considered in conjunction with the accompanying drawings.

BRIEF DESCRIPTION OF THE DRAWINGS

FIG. 4 is a series of curves showing stability of sonicated and unsonicated triethoxycholesterol vesicles; and FIG. 5 is a series of graphs showing therapeutic effect of unsonicated triethoxycholesterol. Vesicles containing encapsulated methotrexate on survival of mice bearing hepatoma 129 ascites tumor.

DESCRIPTION OF THE INVENTION

Figure 1:
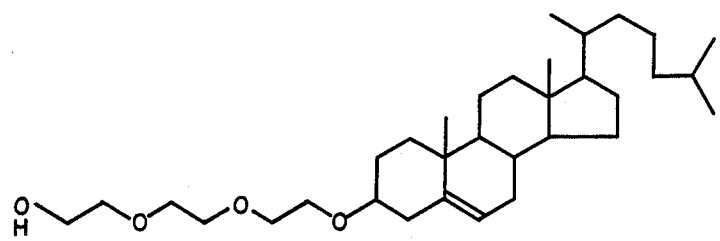
FIG. 1 is a structural formula for 3,6,9-tri-oxaoctan-1-ol-cholesteryl-3ϵ-ol.
Figure 2:
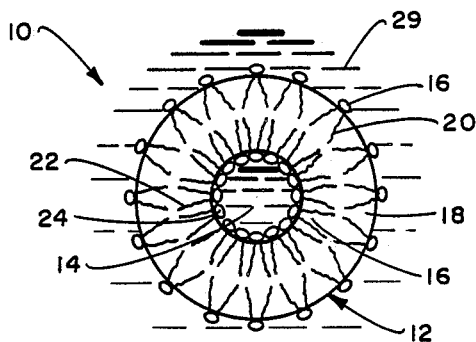
FIG. 2 is a schematic view of a small unilamellar vesicle.

A preferred group of modified cholesterol compounds are formed when R is a polyether side chain terminated with a hydroxyl group. When R is 3,6,9-tri-oxa-octan-1-ol, the cholestryl derivative as shown in FIG. 1 is found to spontaneously form unilamellar vesicles 10 as shown in FIG. 2.

The vesicle 10 contains a single bilayer 12 enveloping an aqueous droplet 14 which may contain a dissolved substance to be dispensed. The single unilamellar vesicle is very small of the order of 200 Å to 3000 Å, usually 500 Å to 1500 Å. The closed, enveloping bilayer 12 is formed of two layers of cholesteryl compounds. Both layers 16, 18 have the rigid, condensed ring cholesterol structure 20, 22 oriented to the inside of the bilayer filling the bilayer volume. The flexible hydrophilic side chains 24, 26 are oriented to the droplet 14 and to the external aqueous phase 29. The vesicle forming molecules can be selected from compounds containing a perhydrocyclopentenophenanthrene nucleus.

Figure 3:
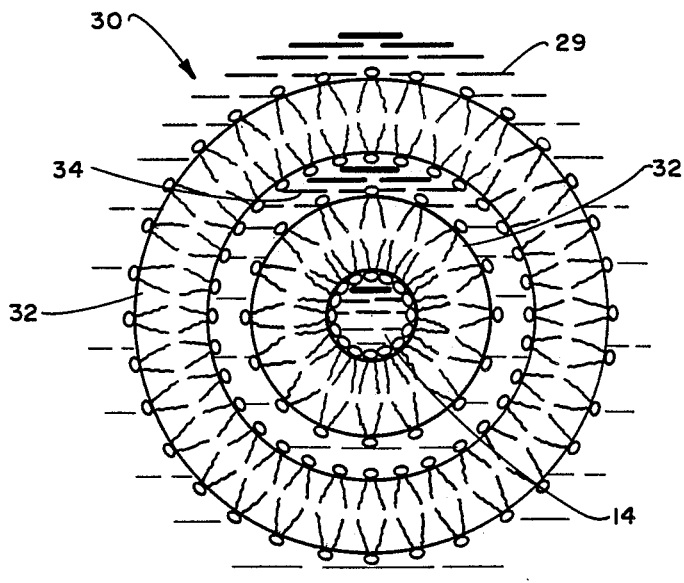
FIG. 3 is a schematic view of a larger multilameler vesicle.

The small, stable, rigid unilamellar vesicles are formed without additional energy. The small size is pharmacologically advantageous since there is a lower uptake of the vesicles by the liver. Also, the absence of sonication permits encapsulation of compounds that would be deactivated by the heat generated by sonication. Sonication of aqueous media containing the 3, 6, 9-trioxa derivative of FIG. 1 results in forming larger multilamellar vesicles 30 as shown in FIG. 3.

The vesicles 30 have diameters from 2500 Å to 5000 Å, generally from 2000 Å to 4000 Å, and have at least two lamellae 32, generally from 2 to 5 lamellae integrated with hydrophilic layers 34. Each lamella 32 is formed of a bilayer 12 as described with reference to FIG. 2.

The other cholesteryl derivatives, having polyether side chains of the formula —(—$OCH_2CH_2$—)-$_m$—$OCH_2CH_2$—OH where m is 1 or 2-3, also spontaneously form stable, rigid unilamellar vesicles with low leakage rates. When m=0, the cholesteryl derivative is surprisingly found to not spontaneously form unilamellar vesicles. The cholesteryl derivatives containing the polyamine side chains can be blended with natural phospholipid forming vesicles to destabilize and increase the leakage rate of the vesicles. The derivative shown in FIG. 1 can be blended with natural phospholipids to stabilize and decrease the leak rate of the liposome-type vesicles.

Many diverse materials can be encapsulated in the unilamellar (SUV) or multilamellar (MLV) vesicles of the invention. Polar, hydrophilic materials are trapped in the aqueous core of the vesicles, while non-polar hydophobic materials can be trapped in the bilayer membrane. Amphophilic materials partition between the core and the bilayer. The encapsulated material can be a household product, a chemical warfare agent, a cosmetic material or a bioaffecting material such as a therapeutic drug such as an antitumor agent, an antimicrobiol agent, such as an antibiotic or an antifungal agent. Cosmetic materials include fragrances, pigments, emollients, humectants and cleansing agents such as compatible surfactants. Household products include insecticide or herbicidal agents, cleaning agents or spot removers.

The concentration of the material depends on the concentration of the vesicles in the aqueous suspension. The concentration of the encapsulated material is usually the same as in current commercial practice for cosmetic or household materials. The concentration of therapeutic substances, the dosage unit and dosage schedule are dependent on the site of delivery and the mode of administration (e.g. IV, IP, etc.). The dosage also depends on other therapeutic substances being co-administered. The mode of administration of liposomes of the invention can be intravenous (IV), interperitoneal (IP), subcutaneous (SC) or any other mode previously utilized with liposomes. The dosage to be utilized is the same as used for the prior unencapsulated use of the same drug or the prior encapsulated use of the same drug in natural or other synthetic liposomes. For example, methotrexate is administered at a rate of 2.5 mg/kg of body weight by IP injection which is about the same dosage administered in unencapsulated form.

The invention will now be illustrated by the following examples of practice. Ethylene glycol was purified by distillation (b.p. 113°-115° C./0.01 mm Hg). Radioactive iron was in the form of $^{59}FeCl_3$ in 0.1 N HCl(1.0 mCi/ml). Dioxane was purified by refluxing over lithium aluminum hydride for several hours followed by distillation prior to use. Thin layer chromatography (TLC) was performed on precoated silica gel 60/Kieselguhr F-254 plates and visualized with $I_2$ or $H_2SO_4$/charring.

Infrared spectra were recorded with a Beckman IR-4240 spectrometer on Nujol mulls. Proton nuclear magnetic resonance ($^1$H-NMR) spectra were obtained on Varian X1-200 or Bruker WM-500 MHz spectrometer. Optical rotations were measured with JASCO DIP-181 digital polarimeter.

Synthesis of 3,6,9-trioxa-octan-1-ol-cholesteryl-3ε-ol (triethoxycholesterol). A solution of cholesteryl p-toluenesulfonate (1 g, 1.85 mmol) in dry dioxane (18 ml) and excess triethylene glycol (7.032 g, 46.8 mmol) was refluxed for 3 h under $N_2$ atmosphere with stirring. TLC analysis indicated that the reaction was completed after 2 h. The reaction mixture was concentrated under reduced pressure (rota vac) to remove dioxane, diluted with water (20 ml), and extracted with ether (50 ml×6). The organic phase was washed with 10 percent aqueous sodium carbonate (10 ml×1), water (15 ml×5) and dried over sodium sulfate. The dried extract was concentrated and dried under vacuum to give a viscous syrup (0.901 g, 92 percent yield). The crude product was pure enough to be used directly without any further purification.

Compounds having the following side chains, R, were prepared according to the above synthetic method:

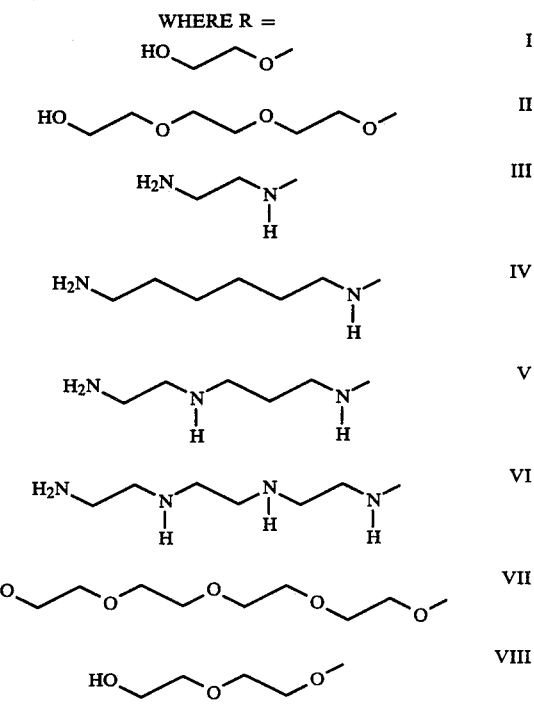

The method for the preparation of the other cholesterol derivatives is essentially the same as that for the synthesis of cholesterol derivative-II (3,6,9-trioxa-octan-1-ol-cholesteryl-3ε-ol). The isolated products were characterized by IR, NMR and TLC and were pure enough to be used directly without further purification. The reactions of cholesteryl p-toluenesulfonate with substrates are summarized in Table 1.

TABLE 1

Summary of Reactions of Cholesteryl P-tolunesufonate with Substrates[a]

| Products[b] (% isolated yield) | Specific Rotation $[\alpha]_D^{25}$ (CHCl$_3$) | IR(neat) $V_{max}$(cm$^{-1}$) | $^1$H-NMR[d](CDCl$_3$, τ) |
|---|---|---|---|
| I (81) | −30.95° | 3470 (medium-weak) 800 (weak) 1110,1060 (medium-weak) | 6.78(m,b,1H,OH) 6.28,6.39(m,4H,CH$_2$O) |
| II (92) | −25.38° | 3460 (strong) 1640 (weak) 865 (medium-strong) 1112 (strong) | 6.84(m,1H,OH) 6.35,6.38(s,12H,CH$_2$O) |
| III (75) | −6.56° | 3310,3370 (medium-weak) 1615 (weak) 800 (medium) 1115 (medium-weak) | 7.34,7.37(m,4H,CH$_2$N) |
| IV (78) | −7.25° | 3380,3310 (weak) 1665 (medium,sharp) 875 (medium, sharp) 1125 (medium-sharp) | 4.74(b,1H,NH) 6.29(s,12H,CH$_2$N) |
| V (65) | −5.0° | 3300 (medium-weak) 1665 (medium-31 sharp) 800 (medium-weak) 1123 (medium-weak) | 4.74(m,b,1H,NH) 6.37,6.38(s,1OH,CH$_2$N) |
| VI (25)[c] | −13.85° | 3300 (medium-weak) 1580 (weak) 1120 (medium-weak) | 6.35,6.38(s,12H,CH$_2$N) |
| VII (64) | | 3450 (medium-strong) 1665 (weak) 1110 (strong) | 6.91(m,1H,OH) 6.85,6.89(s,16H,CH$_2$O) |
| VIII (87) | | 3450 (strong) 1665 (weak) | 6.60(m,1H,OH) 6.37,6.38(s,8H,CH$_2$O) |

TABLE 1-continued

Summary of Reactions of Cholesteryl
P-tolunesufonate with Substrates[a]

| Products[b] (% isolated yield) | Specific Rotation $[\alpha]_D^{25}$ (CHCl₃) | IR(neat) $V_{max}$(cm⁻¹) | ¹H-NMR[d](CDCl₃, τ) |
|---|---|---|---|
| | | 885 (medium-weak) 1125 (strong-broad) | |

[a]Reactions were carried out with 4 mmole cholesteryl p-toluenesulfonate and 25-30 molar equivalents of substrate in refluxing dioxane for 2-4 h under N₂ with stirring.[1]
[b]All isolated products were colorless syrup except I, mp 103-104° C. (petroleum ether, 30-60° C.) Lit.[2] 93-105° and VIII, mp 42-45° C. (petroleum ether, 30-60° C.). IR of I and VIII were taken in Nujol mulls. Isolated products showed a single homogeneous spot on TLC and complete disappearance of starting material cholesteryl-p-toluene-sulfonate and the substrate. TLC was performed in solvent system for products: I ($R_F$0.30) in chloroform, II ($R_F$0.43) in chloroform: ethylacetate (1:1,v/v), III ($R_F$ 0.43) in chloroform: methanol:ammonium hydroxide (2:2:1,v/v), IV ($R_F$ 0.77) in chloroform: meth-anol: ammonium hydroxide (3:2:1,v/v), V ($R_F$ 0.58) and VI ($R_F$ 0.79) in chloroform: methanol: ammonium Hydroxide (2:2:1,v/v).
[c]No attempt was made to obtain maximum yield.
[d]Abbreviations used are s-singlet, d-doublet, m-multiplet, and b-broad. Products I to VIII have similar chemical shifts at 4.50-4.70 (m, 1H; C-6), 9.00-9.07 (s, 3H; C-19), 9.07-9.15 (d, 3H; C-21), 9.12-9.21 (d, 6H; C-26 and C-27), and 9.28-9.38 (s, 3H; C-18).

Preparation of Vesicles

Liposomes containing desferroxamine with a trace amount of ⁵⁹Fe in the aqueous compartment were prepared according to methods described by Patel et al.[1] Dipalmitoyl or distearoyl phosphatidylcholine (PC), cholesterol, and stearylamine, in the molar ratio of 1.54:1.0:0.43, respectively, were dried in a round bottom flask. When liposomes were prepared with various synthetic derivatives, half of their cholesterol amount was replaced with individual cholesterol derivative. An aqueous phase containing 75 mg desferroxamine and a trace amount of ⁵⁹Fe/ml water was added in the flask and stirred for 10 min. The weight ratio of lipids to desferroxamine was approximately 1:2. Liposomes containing dipalmitoyl PC (DPPC) were prepared at 50° C. and distearoyl PC (DSPC) at 60° C. Small unilamellar vesicles were prepared by sonication of the multilamellar vesicles for 30 min. in a water-bath sonicator (Model G11 2SPIT, Laboratory Supplies Co., Hickville, N.Y.). Nonencapsulated ⁵⁹Fe tagged desferroxamine was removed from the vesicles by the method of Fry et al.[3] Liposomes containing ³H-glucose were prepared by a method similar to that for liposomes encapsulated desferroxamine.[3]

[1]Patel, K. R., Li, M. P., Schuh, J. R. and Baldeschwieler, J. D. Biochim. Biophys, Acta. 797, 20-26, (1984).
[3]Fry, D. W., White, J. C. and Goldman, I. D. Anal. Biochem. 90, 809-815 (1978).

The permeability of the vesicles was assessed by the dialysis method. Vesicles, approximately 8-15 mg of total lipids, were suspended in 1 ml of either phosphate buffered saline or fetal calf serum and placed in a dialysis bag. The dialysis bag was placed in 40 ml phosphate buffered saline. Dialysis was carried out at 37° C.; aliquots of the dialysis solution were removed at various times and the percent leakage of the ⁵⁹Fe tagged desferroxamine was determined using a Beckman Biogamma counter.

Injection of Vesicles and Analysis of Radioactivity in Mouse Tissue Samples

Vesicles, approximately 1.5 to 2 mg total lipids, were injected by a single intravenous (IV) injection of 0.2 mil into 2-3 month old Swiss Webster female mice. Groups of mice (4 mice/group) were sacrificed 2 hr after injection. Blood from the jugular vein was collected. The amount of vesicle uptake in the total blood was calculated by presuming that blood comprises 7.3 percent of the total weight of the animals. For bone marrow two rear tibias from each mouse were counted for radioactivity. The amount of vesicle uptake in the total bone marrow was estimated by multiplying the radioactivity in the two tibial segments by a factor of 44. Other tissues were removed and radioactivity was determined with a gamma counter.

Derivatives I, II, VII and VIII have a terminal hydroxyl group and III, IV, V and VI have terminal primary amine groups and different numbers of secondary amine groups. The side chains on derivatives I and III are shorter than on the other derivatives.

Effect of Various Cholesterol Derivatives on the Permeability of DPPC Vesicles.

Table 2 shows the efficiency of encapsulation of the ⁵⁹Fe tagged desferroxamine.

TABLE 2

Effect of Various Cholesterol Derivatives on the Leakage of DF-⁵⁹Fe Encapsulated in Dipalmitoyl Phosphatidylcholine Vesicles

| Lipid Composition[a] | % Encapsulation | Leakage In | % Leakage of DF-⁵⁹Fe Measured by Dialysis Method at 37° C. at Hr | | | | | |
|---|---|---|---|---|---|---|---|---|
| | | | ½ | 1 | 2 | 4 | 19 | 24 |
| Unencapsulated DF-⁵⁹Fe | — | PBS | 33.3 | 55.0 | 77.2 | 91.0 | — | 92.0 |
| | | Serum[b] | 30.0 | 50.0 | 73.2 | 90.4 | — | 93.0 |
| DPPC:CHOL:SA | 3.4 | PBS | 4.3 | 7.8 | 14.8 | 18.8 | — | 21.4 |
| | | Serum | 5.6 | 9.7 | 16.2 | 20.2 | — | 22.4 |
| DPPC:CHOL:CHOL-I:SA | 2.7 | PBS | 0.3 | 2.4 | 2.2 | 2.5 | 3.1 | 3.5 |
| | | Serum | 0.4 | 1.6 | 4.3 | 3.7 | 4.0 | 4.8 |
| DPPC:CHOL:CHOL-II:SA | 4.8 | PBS | 1.9 | 2.2 | 2.3 | 4.0 | 4.1 | — |
| | | Serum | 1.2 | 1.8 | 3.0 | 4.4 | 4.3 | — |
| DPPC:CHOL:CHOL-III:SA | 3.3 | PBS | 7.2 | 10.8 | 12.5 | 15.5 | 14.6 | — |
| | | Serum | 14.2 | 31.7 | 48.0 | 58.1 | 55.7 | — |
| DPPC:CHOL:CHOL-IV:SA | 0.6 | PBS | — | — | — | — | — | — |
| | | Serum | 32.0 | 42.9 | 58.5 | 65.3 | 67.9 | 65.5 |
| DPPC:CHOL:CHOL-V:SA | 0.2 | PBS | — | — | — | — | — | — |

TABLE 2-continued

Effect of Various Cholesterol Derivatives on the Leakage of DF-$^{59}$Fe Encapsulated in Dipalmitoyl Phosphatidylcholine Vesicles

| Lipid Composition[a] | % Encapsulation | Leakage In | % Leakage of DF-$^{59}$Fe Measured by Dialysis Method at 37° C. at Hr | | | | | |
|---|---|---|---|---|---|---|---|---|
| | | | ½ | 1 | 2 | 4 | 19 | 24 |
| | | Serum | 21.9 | 31.3 | 51.4 | 59.3 | 62.3 | 56.8 |
| DPPC:CHOL:CHOL-VI:SA | 0.4 | PBS | 21.9 | 36.9 | 48.0 | 57.0 | 60.9 | 56.5 |
| | | Serum | 23.5 | 49.3 | 64.0 | 66.7 | 70.2 | 68.9 |

[a]Abbreviations: DPPC, dipalmitoyl phosphatidylcholine; CHOL, cholesterol; SA, stearylamine; PBS, phosphate buffered saline pH 7.4, DF, Desferroxamine; 1.54:1:0.43 molar ratio of PC:CHOL:SA; 1.54:0.5:0.5:0.43 molar ratio of PC:CHOL:CHOL derivative:SA.
[b]Fetal calf serum Vesicles prepared in the absence of any derivative or in the presence of derivative I, II, or III were able to encapsulate about 3 to 5 percent of the total desferroxamine. Very poor encapsulation, less than 1 percent of the desferroxamine, resulted when derivatives IV, V, or VI were used.

Table 2 also shows the permeability of $^{59}$Fe tagged desferroxamine from DPPC vesicles. Unencapsulated desferroxamine is lost very rapidly from the dialysis bag (90 percent within 4 hr). The presence of fetal calf serum has no effect on the leakage of unencapsulated desferroxamine from the dialysis bag. Encapsulation of desferroxamine in vesicles prepared from DPPC, cholesterol and stearylamine resulted in significantly less leakage of desferroxamine; thus after 4 hr only 18 to 20 percent of the encapsulated desferroxamine was lost from the vesicles. The presence of serum again had no effect on the permeability of these control vesicles.

As shown in Table 2, the presence of cholesterol derivatives I and II provides reduced permeability of vesicles with a significant reduction in the leakage of desferroxamine. Only 3 to 4 percent of encapsulated desferroxamine was lost at 4 hr. Also serum had no effect on the leakage of vesicles containing cholesterol derivative I or II. The presence of cholesterol derivatives III, IV, V or VI results in very permeable vesicles, with 60 percent of the encapsulated desferroxamine being lost from the vesicles after only 4 hr of dialysis in the presence of serum. However, vesicles prepared with derivative III were less permeable in phosphate buffered saline, and only 15 percent of encapsulated desferroxamine is lost from these vesicles after 4 hr of dialysis.

Effect of Various Choleserol Derivatives on the Permability of DSPC Vesicles.

Table 2 shows that the encapsulation of desferroxamine in vesicles containing cholesterol derivative V or VI is very low, less than 1.0 percent. The encapsulation in the absence of any derivative or in the presence of derivative III or IV is 1 to 4 percent.

DPPC vesicles prepared with cholesterol derivative III, IV, V and VI were very permeable in the presence of serum. In order to reduce the permeability of vesicles, we replaced DPPC with DSPC. As shown in Table 3, the permeability of vesicles prepared with DSPC, cholesterol, and stearylamine was not much different from DPPC vesicles.

TABLE 3

Effect of Various Cholesterol Derivatives on the Leakage of DF-$^{59}$Fe Encapsulated in Distearoyl Phosphatidylcholine Vesicles

| Lipid Composition[a] | % Encapsulation | Leakage In | % Leakage of DF-$^{59}$Fe Measured by Dialysis Method at 37° C. at Hr | | | | | |
|---|---|---|---|---|---|---|---|---|
| | | | ½ | 1 | 2 | 4 | 19 | 24 |
| DSPC:CHOL:SA | 3.6 | PBS | 3.5 | 6.5 | 11.7 | 14.1 | — | 14.6 |
| | | Serum[b] | 3.7 | 6.1 | 11.0 | 13.1 | — | 13.5 |
| DSPC:CHOL:CHOL-III:SA | 2.1 | PBS | 5.7 | 10.2 | 13.0 | 14.7 | 16.1 | 17.2 |
| | | Serum | 10.8 | 15.9 | 19.0 | 21.0 | 21.1 | 22.5 |
| DSPC:CHOL:CHOL-IV:SA | 1.2 | PBS | 5.9 | 8.6 | 9.4 | 11.7 | 14.3 | 15.2 |
| | | Serum | 28.9 | 41.6 | 54.4 | 58.8 | 58.5 | 59.6 |
| DSPC:CHOL:CHOL-V:SA | 0.3 | PBS | — | — | — | — | — | — |
| | | Serum | 28.5 | 38.8 | 39.9 | 50.3 | 51.3 | 53.5 |
| DSPC:CHOL:CHOL-VI:SA | 0.2 | PBS | — | — | — | — | — | — |
| | | Serum | 8.0 | 8.9 | 10.4 | 9.3 | 12.7 | 14.1 |

[a]Abbreviations: DSPC, distearoyl phosphatidylcholine; CHOL, cholesterol; SA, stearylamine; for other abbreviations and molar ratio see Table 2.
[b]Fetal calf serum Also, serum had no effect on the leakage of these vesicles. However, replacing DPPC with DSPC for either cholesterol derivative III or VI containing vesicles results in significantly reduced permeability. The rate of loss of desferroxamine for cholesterol derivative III and VI containing DSPC vesicles is less than half the rate of loss for the corresponding DPPC vesicles. Replacing DPPC with DSPC in cholesterol derivative IV or V containing vesicles has no effect on their leakage in serum. Vesicles prepared with cholesterol derivative III or VI are less permeable in phosphate buffered saline.

Effect of Cholesterol Derivative II on the Leakage of $^3$H-glucose Encapsulated in DPPC Vesicles The results in Table 2 show that replacing half of the cholesterol with cholesterol derivative II reduces the permeability of DPPC vesicles encapsulating desferroxamine. We used $^3$H-glucose to explore these effects with DPPC vesicles with a different tracer encapsulated in the aqueous compartment. Table 4 shows that 68–70 percent of the $^3$H-glucose is lost from the dialysis bag after 4 hr of dialysis and serum has no effect on the leakage of unencapsulated $^3$H-glucose. When DPPC vesicles are used to encapsulate $^3$H-glucose their permeability in phosphate buffered saline is similar to that seen for desferroxamine, with 17 percent of the encapsulated $^3$H-glucose being lost after 4 hr of dialysis. However, when these vesicles are incubated in serum, glucose leakage is 2–2.5 times higher than in phosphate buffered saline. When half of the cholesterol is replaced with a cholesterol-II derivative, the permeability is reduced with vesicles being equally permeable in both phosphate buffered saline and serum and only 11 percent of the glucose leaking out after 4 hr.

Effect of Derivative II or III on the Tissue Distribution of Vesicles in Vivo Table 4 shows the tissue distribution of unencapsulated and liposome encapsulated $^{59}$Fe tagged desferroxamine in mice.

This is accompanied by significantly higher liver uptake.

These results show that vesicles encapsulating desferroxamine prepared either with DPPC or DSPC are equally permeable in phosphate buffered saline or bovine serum. The permeability of vesicles containing DSPC appears to be slightly less than that of DPPC containing vesicles. Similar results have been reported using the x-ray perturbed angular correlation technique. Replacing half of the cholesterol with synthetic deriva-

TABLE 4

Mouse Tissue Distribution at 2 hr After Intravenous Injection of Unencapsulated and Phospholipid Vesicle Encapsulated DF-$^{59}$Fe

| | % INJECTED DOSE OF VESICLES[a] | | | |
|---|---|---|---|---|
| | | Vesicle Composition[b] | | |
| Tissue | Unencapsulated | DSPC:CHOL:SA | DSPC:CHOL:CHOL-II:SA | DSPC:CHOL:CHOL-III:SA |
| Blood[c] | 3.0 ± 0.6 | 54.6 ± 1.4 | 43.3 ± 2.3 | 4.7 ± 0.9 |
| Bone marrow[d] | 4.7 ± 0.9 | 7.9 ± 0.4 | 8.9 ± 1.3 | 5.7 ± 1.2 |
| Heart | 0.1 ± 0.0 | 0.4 ± 0.0 | 0.4 ± 0.0 | 0.1 ± 0.0 |
| Lung | 0.1 ± 0.0 | 0.8 ± 0.1 | 0.7 ± 0.1 | 0.3 ± 0.1 |
| Liver | 1.5 ± 0.2 | 17.3 ± 1.1 | 18.4 ± 0.4 | 41.3 ± 2.0 |
| Small Intestine[e] | 1.1 ± 0.2 | 3.5 ± 0.4 | 2.9 ± 0.2 | 1.3 ± 0.2 |
| Kidney | 0.9 ± 0.1 | 2.1 ± 0.3 | 1.8 ± 0.2 | 0.8 ± 0.2 |
| Spleen | 0.9 ± 0.3 | 1.7 ± 0.3 | 1.5 ± 0.1 | 2.0 ± 0.2 |
| Brain | 0.1 ± 0.0 | 0.2 ± 0.0 | 0.2 ± 0.0 | 0.1 ± 0.0 |
| Stomach[e] | 0.1 ± 0.0 | 0.5 ± 0.1 | 0.4 ± 0.1 | — |
| Large Intestine[e] | 0.9 ± 0.2 | 1.5 ± 0.3 | 2.1 ± 0.4 | — |
| % Recovery | 13.1 ± 4.7 | 90.4 ± 3.0 | 80.7 ± 3.6 | 56.5 ± 3.2 |

[a]Each value represents an average of 4 mice ± the standard error of the mean.
[b]Abbreviations: see Table 3, for molar ratios see Table 2.
[c]Amount of radioactivity in total blood was obtained by presuming that blood comprises 7.3% of the total weight of the animals.
[d]Amount of radioactivity in total marrow was obtained by multiplying the amount of radioactivity measured in the marrow of a pair of tibias by the factor of 44.
[e]Values are calculated including internal contents.

Unencapsulated desferroxamine is removed from the body very rapidly and only 13.1 percent of the injected dose is recovered from blood, bone marrow, heart, lung, liver, small and large intestine, spleen, kidneys, stomach and brain. However, encapsulation of desferroxamine in vesicles results in 60 to 90 percent recovery of desferroxamine from the above organs. At 2 hr after intravenous injection 54.5 percent of the injected dose of vesicles was still circulating in the blood, and 7.9 percent and 17.3 percent of the injected dose of vesicles was recovered from bone marrow and liver, respectively. Replacing half the cholesterol with cholesterol-II reduces the permeability of vesicles (Tables 2 and 5).

tives having a hydroxyl terminal group on the side chain (I and II) reduces the permeability of DPPC vesicles. However, addition of synthetic derivatives with terminal amino groups (III, IV, V and VI) increases the permeability of DPPC vesicles. The four amino-containing derivatives also caused marked permeability differences. This behavior appears to correlate with the length of the groups separating the terminal amine from the sterol nucleus. Thus, the ten-bond derivative VI in DPPC vesicles was very permeable in both phosphate buffered saline and serum, encapsulating only 0.4 percent of the desferroxamine, while the shortest (four-bonds) derivative III encapsulated 3.3 percent and was as permeable as the control vesicles in phosphate buff-

TABLE 5

Effect of Cholesterol-II Derivative on the Leakage of $^3$H-glucose Encapsulated in Dipalmitoyl Phosphatidylcholine Vesticles

| Lipid Composition[a] | % Encapsulation | Leakage in | % Leakage of $^3$H-glucose Measured by Dialysis Method at 37° C. at hr | | | | | |
|---|---|---|---|---|---|---|---|---|
| | | | ½ | 1 | 2 | 4 | 19 | 24 |
| Unencapsulated[a] $^3$H-glucose | — | PBS | 44.6 | 63.8 | 68.5 | 67.8 | 65.4 | 67.0 |
| | | Serum[b] | 47.4 | 63.2 | 69.8 | 69.1 | 66.7 | 69.2 |
| DPPC:CHOL:SA | 4.1 | PBS | 4.6 | 6.9 | 12.8 | 17.4 | 29.4 | 33.3 |
| | | Serum | 9.1 | 18.4 | 32.9 | 43.4 | 52.4 | 53.5 |
| DPPC:CHOL:CHOL-II:SA | 2.9 | PBS | 4.0 | 5.4 | 8.9 | 10.5 | 21.5 | 22.8 |
| | | Serum | 3.3 | 5.7 | 9.4 | 11.1 | 20.6 | 22.1 |

[a]For abbreviations and molar ratios: see Table 2.
[b]fetal calf serum

However, Table 4 shows that cholesterol II has no effect on the tissue distribution of vesicles. When half of the cholesterol is replaced with derivative III three major differences in tissue distribution are observed. The total recovery of encapsulated desferroxamine in cholesterol III containing vesicles is only 56.5 percent among all these organs. Also, cholesterol III containing vesicles are removed very rapidly from the blood, with 4.7 percent of the initial dose in the blood after 2 hr.

ered saline, although markedly permeable in serum. The two eight-bond derivatives (IV and V) behaved similarly to the ten-bond derivative VI. The poor encapsulation and higher permeability of the longer derivatives may relate to either steric effects or charge interactions with the phospholipids or serum proteins. The greater spacer length of these derivatives could result in longer range, more stable electrostatic interactions among neighboring lipid phosphate groups and the aminocholesterol moiety. Such effects could influence the lipid distribution related to volume effects and inside/outside ratios, possibly introducing instability through defect formation or perturbations in bilayer elasticity. The decrease in phosphate buffered saline permeability and increase in the volume of encapsulation seen for the short chain derivative III could be the result of weaker electrostatic interactions, allowing the lipids greater motional freedom to form a more stable bilayer structure. The higher permeability of derivative III containing vesicles in serum is overcome when the higher melting DSPC is used (see Table 3). This result may be related to an increase in vesicle size thus reducing strain, or a decrease in fluidity which has been shown to modulate vesicle-protein interactions such as vesicle lysis by the serum complement system.

The marked reduction in vesicle permeability seen when hydroxylated cholesterol analogs are used may be due to improved steric interactions at the vesicle surface. A role for lipid shape in determining membrane structure has long been considered important. The large, hydrophilic "headgroups" of derivative I and II may provide a better balance than cholesterol for interacting with the phospholipids in the highly curved vesicle outer surface. In fact, derivative II alone has been found to form stable membranes in aqueous solutions. Consistent with this explanation is the observation that the reduced permeability is independent of the medium (either phosphate buffered saline or serum), as would be expected for vesicles intrinsically stabilized by better lipid packing. It is interesting that the leakage of glucose was found to be more rapid than desferroxamine for both control and derivative II containing vesicles (Table 5). The most likely explanation for this observation is that the reduced size and charge neutrality of glucose, relative to desferroxamine, allows the former to pass through the bilayer more easily. The large difference in leakage between phosphate buffered saline and serum for the control vesicles indicates some additional perturbation induced by the serum proteins, while for the stabilized derivative II containing vesicles the increased leakage is the same in both media, consistant with the physical differences between glucose and desferroxamine.

The tissue distribution results indicate that desferroxamine injected by the intravenous route is removed rapidly from the body. However, within the same time period, most of the vesicle encapsulated desferroxamine is recovered. The presence of derivative II has no effect on the tissue distribution of vesicles. However, the presence of III, the four-bond amine containing derivative, drastically alters the tissue distribution of vesicles. These vesicles are cleared from the blood much faster than control vesicles. Such a rapid blood clearance is accompanied by a higher liver uptake.

It is possible that the more cationic derivative III containing vesicles are also taken up more rapidly by phagocytic cells.

The lack of effect that derivative II containing vesicles have on the tissue distribution and rate of blood clearance is consistent with the in vitro observation that this derivative reduces the permeability of the vesicle. The practical development of vesicles for in vivo drug delivery requires that stable formulations be developed in order to provide sufficient shelf-life for such systems to be economically feasible. The study of molecules, such as derivative II, which intrinsically stabilize vesicles without affecting their in vivo tissue distribution, should prove useful in complementing the development of formulations for targeted vesicle systems.

The product triethyoxycholesterol (FIG. 1) showed single homogeneous spot ($R_F$ 0.43) on TLC (chloroform/ethyl acetate, 1:1, v/v/) and complete disappearance of starting material cholesteryl p-toluenesulfonate ($R_F$ 0.88); infrared (Nujol mull): $V_{max}$ 3440 (strong, OH), 1650 and 798 (weak and medium-weak, respectively, C=C), and 1115 cm$^{-1}$ (strong, C—O); specific rotation; $[\alpha]_D^{25} = -25.3°$ (chloroform); $^1$H—NMR (CDCl$_3$); 6.35 and 6.38 (s, 12H, CH$_2$O), 4.68 (m, 1H, C-6), 6.84 (m, 1H, C-3), 7.37 (broad, 1H, OH) 9.03 (s, 3H, C-19), 9.14 (d, 3H, C-21), 9.18 (d, 6H, C-26 and C-27), and 9.35 (s, 3H, C-18).

Preparation of liposomes. Liposomes containing desferroxamine with a trace amount of $^{59}$Fe-desferroxamine in the aqueous compartment were prepared with some modification of the method described by Guilmette et al.[4] Triethoxycholesterol (30 mg), dissolved in chloroform, was added to a 50 ml flask. The chloroform was then removed by vacuum evaporation. An aqueous solution of $^{59}$Fe-desferroxamine (75 mg/ml water) was added to the flask at room temperature and liposomes were prepared by stirring with a magnetic stirring bar. Unencapsulated $^{59}$Fe-desferroxamine from unsonicated liposomes was removed by three successive centrifugations at 3015×g for 10 min, following dilution in phosphate-buffered saline, pH 7.4. Sonication of these liposomes (before removing unencapsulated $^{59}$Fe-desferroxamine) was carried out for 30 min at room temperature in a bath sonicator (model G112SP1T, Laboratory Supplies Co., Inc. Hicksville, N.Y.). Unencapsulated $^{59}$Fe-desferroxamine from sonicated liposomes was removed by the method of Fry et al.[3] Liposomes were negatively stained with 2 percent phosphotungstic acid, pH 7.2 and observed with a Philips 301G transmission electron microscope. Phospholipid liposomes were prepared by a method similar to that used for non-phospholipid liposomes. Liposome preparation was carried out at 60° C. The molar ratio of distearoylphosphatidylcholine, cholesterol, and stearylamine was 1.5:1:0.3. Encapsulation of methotrexate in non-phospholipid liposomes was carried out by adding 50 mg methotrexate/ml solution in 30 mg dried film of triethoxycholesterol. Free methotrexate was removed by centrifugation procedure as described earlier.

[4] Guilmette, R. A., Cerny, E. A., Rahman, Y. E. Life Sci. 22, 313-320 (1978).
[3] Fry, D. W., White, J. C. and Goldman, I. D. Anal. Biochem. 90, 809-815 (1978).

Liposome stability. The stability of unsonicated and sonicated liposomes was determined by dialysis. Liposomes suspended in 1 ml of phosphate-buffered saline or fetal calf serum, were placed in 40 ml of phosphate-buffered saline. Dialysis was carried out in phosphate-buffered saline at 37° C. Aliquots of the external solution were removed at various times and the percent of $^{59}$Fe-desferroxamine that had leaked out was measured in a Beckman Biogamma Counter.

Injection of liposomes and analysis of $^{59}$Fe-desferroxamine radioactivity in mouse tissue samples. Lipsomes were administered by a single intravenous injection of 0.2 ml into female Swiss-Webster mice (2–3 months old). Groups of mice (4 each) were killed 2 h after injection. The amount of liposomes present in the blood was calculated by assuming that blood comprised 7.3 percent of the total body weight. For bone marrow determination both tibias from each mouse were counted, and this value was multiplied by 44. Other tissues were removed and total radioactivity was measured directly.

Maintenance of hepatoma 129 ascites tumor. An ascites form of hepatoma 129 was obtained from DCT Tumor Bank, Worcester, Mass. The tumor was maintained in C3H mice by serial intraperitoneal injection every 14 days of 0.2 to 0.3 ml of undiluted ascites fluid.

In vivo treatment of mice bearing hepatoma 129 ascites tumor. Hepatoma 129 cells used in each comparative treatment study were all taken aseptically from a single C3H mouse. Seven-day-old tumor cells were filtered through two layers of cotton gauze, counted using hemocytometer and diluted in phosphate-buffered saline. 3–4 month-old C3H mice were each injected intraperitoneally with $1 \cdot 10^6$ viable cells in 0.2 ml. After 24 h, these mice were given methotrexate in unencapsulated (3 mg/kg body weight) or unsonicated triethoxycholesterol liposome-encapsulated (2.5 mg/kg body weight) forms by intraperitoneal injection. The mean survival times of the mice were then calculated.

Lipsome structure and stability. FIG. 4 shows the stability of unsonicated and sonicated triethyoxcholesterol liposomes. Both preparations were capable of encapsulating about 1.0 percent of the $^{59}$Fe-desferroxamine present. Unsonicated liposomes were stable in phosphate-buffered saline and more leaky in serum. After 19 h, only 0.3 percent of encapsulated $^{59}$Fe-desferroxamine leaked out in phosphate-buffered saline, while 14.0 percent was released in serum. Initial release of encapsulated material was rapid for sonicated liposomes in either phosphate-buffered saline or serum. However, after 4 h the rate of leakage was markedly slower.

Negatively stained electron micrographs of unsonicated and sonicated triethoxycholesterol liposomes. Unlike phospholipids, sonication of triethoxycholesterol liposomes has little effect on the average liposome diameter, with unsonicated liposomes having a value of 103±48 nm and sonicated liposomes having a value of 165±59 nm. No lamellar structures were discerned in unsonicated triethoxycholesterol liposomes. However, sonication resulted in the formation of multilayered lamellar structures.

Tissue distribution of liposomes. The tissue distributions for liposome-encapsulated and unencapsulated $^{59}$Fe-desferroxamine in mice, 2 h after intraveneous administration, are shown in Table 6.

TABLE 6

MOUSE TISSUE DISTRIBUTION OF 2 h AFTER INTRAVENOUS INJECTION OF UNENCAPSULATED AND LIPOSOME-ENCAPSULATED $^{59}$Fe$^1$ Desferroxamine Each value represents an average of 4 mice ± the standard error of the mean. Amount of radioactivity in total blood was obtained by presuming that blood comprises 7.3% of the total weight of the animals. Amount of radioactivity in total marrow was obtained by multiplying the amount of radioactivity measured in the marrow of a pair of tibias by the factor of 44

| Tissue | % Injected dose of liposomes | | | | |
| --- | --- | --- | --- | --- | --- |
| | Unencapsulated $^{59}$Fe-deferoxamine | Unsonicated triethoxycholesterol liposomes | Unsonicated phospholipid liposomes | Sonicated triethoxycholesterol liposomes | Sonicated phospholipid liposomes |
| Blood | 3.0 ± 0.6 | 9.5 ± 4.5 | 1.1 ± 0.4 | 10.8 ± 2.9 | 54.6 ± 1.4 |
| Bone marrow | 4.7 ± 0.9 | 6.8 ± 0.7 | 10.9 ± 1.5 | 6.4 ± 1.6 | 7.9 ± 0.4 |
| Heart | 0.1 ± 0.0 | 0.1 ± 0.0 | 0.4 ± 0.0 | 0.1 ± 0.0 | 0.4 ± 0.0 |
| Lung | 1.5 ± 0.2 | 1.4 ± 0.3 | 8.2 ± 0.5 | 0.4 ± 0.1 | 0.8 ± 0.1 |
| Liver | 1.5 ± 0.2 | 54.9 ± 7.2 | 59.9 ± 2.8 | 31.1 ± 5.8 | 17.3 ± 1.1 |
| Small Intestine[a] | 1.1 ± 0.2 | 2.9 ± 1.0 | 0.7 ± 0.1 | 1.8 ± 0.2 | 3.5 ± 0.4 |
| Kidney | 0.9 ± 0.1 | 0.5 ± 0.1 | 1.2 ± 0.2 | 0.8 ± 0.1 | 2.1 ± 0.3 |
| Spleen | 0.9 ± 0.3 | 20.2 ± 3.7 | 7.3 ± 1.4 | 8.7 ± 2.4 | 1.7 ± 0.3 |
| Brain | 0.1 ± 0.0 | 0.1 ± 0.0 | 0.2 ± 0 | 0.1 ± 0.0 | 0.2 ± 0.0 |
| Stomach[a] | 0.1 ± 0.0 | 0.8 ± 0.5 | 0.3 ± 0.1 | 0.2 ± 0.1 | 0.5 ± 0.1 |
| Large Intestine[a] | 0.9 ± 0.2 | 0.9 ± 0.2 | 0.2 ± 0.0 | 0.8 ± 0.2 | 1.5 ± 0.3 |
| % Recovery of injected dose | 14.8 ± 4.8 | 98.1 ± 1.8 | 90.4 ± 0.8 | 61.2 ± 1.2 | 90.5 ± 3.0 |

[a]Values are calculated including internal contents.

Little or no significant amounts of $^{59}$Fe-desferroxamine could be found in the major tissues (liver, spleen, lung and bone marrow), when unencapsulated material was injected. Most of the label encapsulated in small, sonicated phospholipid liposomes remained in the circulation after 2 h, with significant amounts also accumulating in the liver and bone marrow. The unsonicated triethoxycholesterol liposomes and the unsonicated phospholipid liposomes showed a much different tissue distribution. Most of the label for sonicated and unsonicated triethoxycholesterol, and unsonicated phospholipid liposomes preparations appeared in the liver after 2 h. Significant amounts of these three preparations were also found in the bone marrow and spleen, with a higher spleen concentration found for unsonicated triethoxycholesterol liposomes. Despite a broad variation, large amounts of triethoxycholesterol encapsulated material remained in the circulation after 2 h, while for phospholipid liposomes, a higher accumulation was found in the lungs, relative to the triethoxycholesterol preparations.

Pharmacological efficacy of triethoxycholesterol liposomes. Untreated hepatoma ascites bearing mice had an average survival time of 15 days (FIG. 5). No significant increase in the average survival time was found for tumor-bearing mice receiving free methotrexate (3 mg/kg body weight) administered by intraperitoneal injection. However, following a single injection of methotrexate (2.5 mg/kg body weight) encapsulated in unsonicated triethoxycholesterol liposomes, the average survival time increased to 29.1 days.

The results presented here show that a cholesterol derivative, in the absence of any phospholipids, can form stable liposomes capable of encapsulating polar compounds. However, unlike phospholipid liposomes the triethoxycholesterol liposomes, when sonicated, do not become small, unilamellar vesicles but rather form large, multilamellar arrays. The presence of lamellar structures was not detected in the unsonicated triethoxycholesterol liposomes, though both phases were capable of encapsulating polar compounds, thus indicating that hydrated triethoxycholesterol forms structures having two polar surfaces separated by a hydrophobic region. Brockerhoff and Ramsammy[5] described their finds for a cholesterol-poly(ethylene glycol) derivative which also forms closed, multilamellar dispersion in aqueous solvents.

[5] Brokerhoff, H. and Ramsammy, L. *Biochim. Biophys. Acta.* 691, 227–232 (1982).

Stability studies, carried out in serum and phosphate-buffered saline, show a rapid leakage in the first few hours for sonicated triethoxycholesterol liposomes. Since little or no encapsulated material is released subsequent to the initial loss of 15 percent, it seems likely that this observation is due to the presence of an inherently unstable fraction of the sonicated liposome population. The relative instability seen for unsonicated triethoxycholesterol liposomes in serum, compared to phosphate-buffered saline, may be due to lipid exchange or fusion, possibly involving lipoproteins or an enzymatic activity. Such perturbations could result in local defects, which have been shown to destabilize phospholipid vesicles.

Following intravenous administration of liposomes containing $^{59}$Fe-desferroxamine both phospholipid and triethoxycholesterol suspensions were rapidly cleared from the circulation. However, for small, sonicated phospholipid liposomes, more than half of the labeled material was still present in the blood after 2 h. This indicates that liposome size, in addition to chemical composition, is important in determining the rate of tissue uptake. The slightly increased uptake of triethoxycholesterol liposomes by the spleen may be related to a reduced elastic modulus of curvature, relative to the more flexible phospholipid bilayer system. This would give rise to a decrease in the deformability of triethoxycholesterol liposomes which might make them more susceptible to uptake by the spleen.

The pharmacological efficacy of triethoxycholesterol liposomes is clearly demonstrated in FIG. 5. The increased potency of encapsulated methotrexate, in prolonging the survival time of mice bearing ascites tumors, shows that triethoxycholesterol liposomes can effectively release drugs in vivo, similar to results reported for phospholipid containing systems. These studies indicate that alternative amphiphilic compounds, bearing little resemblance to naturally occurring bilayer forming systems, can be successfully used to encapsulate and potentiate pharmacologically effective agents.

A further study demonstrated that a combination of immunotherapy with triethoxycholesterol liposome chemotherapy can provide improved results compared with either therapy alone. Efficacy studies of triethoxycholesterol encapsulated (LA) amphotericin B and a nonliposome associated (NLA) form of the same drug were conducted in vivo and in vitro Histoplasmosis models.

Use of this liposome for treating fungal infections had not been previously done. In vivo studies, C57B1/6J mice were inoculated intraperitoneally (IP) with 48 h old yeast cells of *Histoplasma capsulatum*. When infection was established, some mice were inoculated intravenously (IV) two or three times with 0.35 mg/kg NLA drug (more than 0.35 mg/kg NLA drug caused death of some mice); other mice were treated with either 0.35 mg/kg, 2 mg/kg or 4 mg/kg LA drug. Mice were sacrificed 14 days following infection, their spleens weighed, homogenized, and colony forming units XCFU/spleen determined. Peritoneal macrophages from uninfected mice, cultured in vitro, were challenged with fungus; some cells were treated with different concentrations of LA, others were treated with NLA drug. The number of yeast/macrophage was determined at different incubation times. Results showed that CFU/spleen of mice given 0.35 mg/kg LA or NLA drug were similar ($4-6 \times 10^2$ CFU/spleen); treatment with 2 mg/kg or 4 mg/kg of LA drug yielded no CFU when mice were infected with $1.5 \times 10^8$ yeast cells. No yeast could be seen in cultured macrophases 22.5 h after treatment with as little as 5 µg LA or NLA drug; nondrug treated macrophages contained 5 yeast/cell at this time. In conclusion, although use of either LA or NLA drug at the same concentration gave similar results, only LA drug could be given in vivo in sufficient concentrations to eliminate CFU from the spleen.

It is to be realized that only preferred embodiments of the invention have been described and that numerous substitutions, modifications and alterations are permissible without departing from the spirit and scope of the invention as defined in the following claims.

We claim:

1. A unilamellar, closed vesicle having a diameter from 200 Angstroms to 3,000 Angstroms spontaneously formed by combining a triethoxy cholesterol with water in absence of sonication.

2. A vesicle according to claim 1 in which the cholesterol is 3,6,9-trioxa-octan-1-ol-cholesteryl-3ϵ-ol.

3. A vesicle according to claim 2 in which the diameter of the vesicle is from 500 Angstroms to 1500 Angstroms.

4. A vesicle according to claim 3 in which the water contains a dissolved compound.

5. A vesicle according to claim 4 in which the dissolved compound is a pharmaceutical.

6. A vesicle according to claim 5 in which the compound is an antitumor compound.

7. A vesicle according to claim 5 in which the compound is an antifungal agent.

8. A method of forming a vesicle comprising the step of:

combining triethoxy cholesterol with water in absence of sonication to spontaneously form unilamellar, closed vesicles having a diameter from 200 Angstroms to 3,000 Angstroms.

9. A method according to claim 8 in which water is added to a dried film of the cholesterol to spontaneously form said vesicles.

10. A method according to claim 9 in which the cholesterol is 3,6,9-trioxa-octan-1-ol-cholesteryl-3ϵ-ol.

11. A method according to claim 8 in which the water contains a dissolved compound.

12. A method according to claim 1 in which the dissolved compound is a pharmaceutical.

13. A method according to claim 11 in which the compound is an antitumor compound or an antifungal agent.

* * * * *